(12) United States Patent
Loiseau et al.

(10) Patent No.: US 8,907,114 B2
(45) Date of Patent: Dec. 9, 2014

(54) METHOD FOR PREPARING METAL-ORGANIC FRAMEWORK CRYSTALLISED AND POROUS ALUMINIUM AROMATIC AZOCARBOXYLATES

(75) Inventors: Thierry Loiseau, Marcqen-Baroeul (FR); Gérard Ferey, Paris (FR); Christophe Volkringer, Thal-Marmoutier (FR); Francis Taulelle, Strasbourg (FR); Mohamed Haouas, Fontenay-le-Fleury (FR)

(73) Assignees: Centre National de la Recherche Scientifique—CNRS—, Paris (FR); Universite de Versailles—Saint Quentin en Yvelines, Versailles (FR)

( * ) Notice: Subject to any disclaimer, the term of this patent is extended or adjusted under 35 U.S.C. 154(b) by 344 days.

(21) Appl. No.: 13/129,733

(22) PCT Filed: Nov. 17, 2009

(86) PCT No.: PCT/FR2009/052209
§ 371 (c)(1),
(2), (4) Date: Sep. 9, 2011

(87) PCT Pub. No.: WO2010/058124
PCT Pub. Date: May 27, 2010

(65) Prior Publication Data
US 2011/0319604 A1  Dec. 29, 2011

(30) Foreign Application Priority Data
Nov. 18, 2008 (FR) .................................. 08 06448

(51) Int. Cl.
*C07F 5/06* (2006.01)

(52) U.S. Cl.
CPC ..................................... *C07F 5/069* (2013.01)
USPC .......................................................... 556/27

(58) Field of Classification Search
USPC ........................................... 534/602; 556/27
See application file for complete search history.

(56) References Cited

FOREIGN PATENT DOCUMENTS

| DE | 10 2005 053 430 A1 | 11/2005 |
|---|---|---|
| WO | WO 02/088148 A1 | 11/2002 |
| WO | WO 2006/050898 A1 | 5/2006 |
| WO | WO 2006/110740 A2 | 10/2006 |
| WO | WO 2007/023119 A1 | 3/2007 |
| WO | WO 2007/023134 A1 | 3/2007 |
| WO | WO 2007/118841 A2 | 10/2007 |
| WO | WO 2007/128994 A1 | 11/2007 |

OTHER PUBLICATIONS

Volkringer et al., Letters, Nature Materials, Advance online publication, 2007.*
Bourrelly, S. et al. "Different Adsorption Behaviors of Methane and Carbon Dioxide in the Isotypic Nanoporous Metal Terephthalates MIL-53 and MIL-47". J. Am. Chem. Soc., 127, 13519-13521 (2005).
Chen, B. et al. "A Triply Interpenetrated Microporous Metal-Organic Framework for Selective Sorption of Gas Molecules". Inorganic Chemistry, 46, 21, 8490-8492 (2007).
Chui, S.S. et al. "A Chemically Functionalizable Nanoporous Material [Cu3(TMA)2(H2O)3]n". Science, 283, 1148-1150 (1999).
Eddaoudi, M. et al. "Systematic Design of Pore Size and Functionality in Isoreticular MOFs and Their Application in Methane Storage". Science, 295, 469-472 (2002).
Ferey, G. et . "Hybrid Porous Solids: Past, Present, Future". Chem. Soc. Rev., 37, 191-214 (2008).
Ferey, G. et al. "Hydrogen Adsorption in the Nanoporous Metal-benzenedicarboxylate M(OH)(O2C—C6H4—CO2) (M = Al3+, Cr3+), MIL-53". Chem. Commun., 2976-2977 (2003).
Henschel, A. et al. "Catalytic properties of MIL-101". Chem. Commun. 4192-4194 (2008).
Horcajada, P. et al. "Metal-Organic Frameworks as Efficient Materials for Drug Delivery". Angew. Chem. Int. Ed., 45, 5974-5978 (2006).
Horcajada, P. et al. "Synthesis and catalytic properties of MIL-100(Fe), an iron(III) carboxylate with large pores". Chem. Commun. 2820-2822 (2007).
Hwang, Y.K. et al. "Amine Grafting on Coordinatively Unsaturated Metal Centers of MOFs: Consequences for Catalysis and Metal Encapsulation". Angew. Chem. Int. Ed. 47, 4144-4148 (2008).
Kitagawa, S. et . "Functional Porous Coordination Polymers". Angew. Chem. Int. Ed., 43, 2334-75 (2004).
Latroche, M. et al. "Hydrogen Storage in the Giant-Pore Metal-Organic Frameworks MIL-100 and MIL-101". Angew. Chem. Int. Ed., 45, 8227-8231 (2006).
Lee, Y.G. "A Comparison of the H2 Sorption capacities of Isostructural Metal-Organic Frameworks With and Without accessible Metal Sites: [{Zn2(abtc)(dmf)2}3] and [{Cu2(abtc)(dmf)2}3] versus [{Cu2(abtc)}3]". Angew Chem Int. Ed, 47, 7741-7745 (2008).
Li, H. et al. "Design and Synthesis of an Exceptionally Stable and Highly Porous Metal-Organic Framework". Nature, 402, 276-269 (1999).

(Continued)

*Primary Examiner* — Yong Chu
*Assistant Examiner* — Sonya Wright
(74) *Attorney, Agent, or Firm* — Arent Fox LLP

(57) ABSTRACT

The present invention relates to a method for preparing an MOF solid of a crystallised and porous aluminium aromatic azocarboxylate, in a non-aqueous organic medium. The invention also relates to solids made up of metal-organic frameworks (MOF) of aluminium aromatic azocarboxylates capable of being obtained by the method of the invention, as well as to the uses thereof for the storage of liquid or gaseous molecules, for selective separation of gas and for catalysis.

11 Claims, 6 Drawing Sheets

(56) References Cited

OTHER PUBLICATIONS

Llewellyn, P.L. et al. "How Hydration Drastically Improves Adsorption Selectivity for CO2 over CH4 in the Flexible Chromium Terephthalate MIL-53". Angew. Chem. Int. Ed. 45, 7751-7754 (2006).

Loiseau, T. et al. "A Rationale for the Large Breathing of the Porous Aluminum Terephthalate (MIL-53) Upon Hydration". Chem. Eur. J., 10, 1373-1382 (2004).

Loiseau, T. et al. "Hydrothermal Synthesis and Crystal Structure of a New Three-Dimensional Aluminum-Organic Framework MIL-69 with 2,6-Naphthalenedicarboxylate (ndc), Al(OH)(ndc) • H2O". C.R. Chimie, 8, 765-772 (2005).

Loiseau, T. et al. "MIL-96, a Porous Aluminum Trimesate 3D Structure Constructed from a Hexagonal Network of 18-Membered Rings and µ3-Oxo-Centered Trinuclear Units". J. Am. Chem. Soc., 128, 10223-10230 (2006).

Müller, U. et al. "Metal-Organic Frameworks—Prospective Industrial Applications". J. Mater. Chem., 16, 626-636 (2006).

Rosi, N.L. et al. "Hydrogen Storage in Microporous Metal-Organic Frameworks". Science, 300, 1127-1129 (2003).

Volkringer, C. et al. "A Microdiffraction Set-up for Nanoporous Metal-Organic-Framework-Type Solids". Nature Materials, 6, 760-764 (2007).

Yaghi, O.M. et al. "Reticular Synthesis and the Design of New Materials"; Nature, 423, 705-14 (2003).

Loiseau, Thierry et al., "MIL-96, a Porous Aluminum Trimesate 3D Structure Constructed from a Hexaganol Network of 18-Membered Rings and .mu.3-Oxo-Centered Trinuclear Units", Journal of the American Chemical Society, 2006, pp. 10223-10230, vol. 128(31).

Lee, Yong-Gon et al., "A Comparison of the H2 Sorption Capacities of Isostructural Metal-Organic Frameworks with and without Accessible Metal Sites: [{Zn2(abtc)(dmf)2}3] and [{Cu2(abtc)(dmf)2}3] versus [{Cu2(abtc)}3]", Angewandte Chemie, International Edition, 2008, pp. 7741-7745, vol. 47(40).

Chen, Banglin et al., "A triply Interpenetrated Microporous Metal-Organic Framework for Selective Sorption of Gas Molecules", Inorganic Chemistry, 2007, pp. 8490-8492, vol. 46(21).

* cited by examiner

METHOD FOR PREPARING METAL-ORGANIC FRAMEWORK CRYSTALLISED AND POROUS ALUMINIUM AROMATIC AZOCARBOXYLATES

TECHNICAL FIELD

The present invention relates to a method for preparing an MOF solid of a crystallized and porous aluminum aromatic azocarboxylate, in a nonaqueous organic medium.

It also relates to solids made up of metal-organic frameworks (MOF) of aluminum aromatic azocarboxylates that may be obtained by the method of the invention as well as to their uses for the storage of liquid or gaseous molecules, for selective gas separation and catalysis.

In the description below, the references between brackets [ ] refer to the list of references presented at the end of the text.

RELATED ART

Metal-organic Frameworks (MOF) constitute a new class of microporous solids (or even mesoporous for part of them). It relies on the concept of a three-dimensional assembly of rigid organic ligands (comprising a benzene ring, for example) with metal centers. The latter can be arranged to form isolated clusters, infinite chains or inorganic layers which connect to each other through the organic ligands via carboxylate or amine type connections. Several groups Yaghi [1], Kitagawa [2] and Férey [3], have exposed this kind of strategy for forming crystallized solids providing three-dimensional frames with exceptional porosity properties (BET surface area>3000 $m^2 \cdot g^{-1}$).

Usually, this kind of materials is characterized by the specific surface area thereof (giving a precise idea of their accessible porosity for incorporating molecules). These specific surface area values (expressed in $m^2$ per gram of material) are measured by the Brunauer-Emmett-Teller (or BET) methods which makes it possible to examine the surface of the pores by chemisorption of nitrogen at 77 K (multilayer model) or Langmuir which uses the same process with a single layer model. These new materials prove to be very good adsorbents for gases such as hydrogen [4-6], methane [7, 8] or carbon dioxide [8]. Thus, they can replace activated carbons or zeolites. Moreover, this kind of solids (some of which being biocompatible) may have applications for encapsulating and controlled salting out of medicated molecules [9].

From an industrial valorization standpoint, several research groups have particularly focused their researches on this new emergent class of porous materials. Indeed, the German company BASF (Ludwigshafen, Germany) and the Yaghi Group (UCLA, the USA) have developed the synthesis processes and the forming of new solids essentially based on divalent (1st series of alkaline-earth transition metals) or trivalent (rare earths) elements combining organic ligands (mainly aromatic carboxylates) [10, 11].

Methods for preparing solids incorporating metals such as for example aluminum and zinc and organic ligands such as for example terephtalic acid, trimesic acid, naphthalene-2,6-dicarboxylic acid have also been described [12, 13].

For more than ten years, the team of Gérard Férey (Versailles) focused on the synthesis and the characterization of Metal-Organic Framework (MOF) type porous solids by developing several research directions [3], in particular the synthesis of MOF solids incorporating aluminum. In particular, the synthesis of crystallized porous aluminum carboxylates such as for example aluminum terephthalate MIL-53 [14], aluminum naphthalate MIL-69 [15] and aluminum trimesates MIL-96 [16] and MIL-110 [17] have been described. Mil-n means Materials of the Lavoisier Institute (Materiaux de l'Institut Lavoisier in French). Some of these solids have very interesting adsorption capacities [5, 8] for gases ($H_2$, $CO_2$, $CH_4$).

It should be noted that two other materials of the series, zinc terephthalate MOF-5 [18] and copper trimestate HKUST-1 [19] have also been described.

Other materials were obtained with terephtalic acid under other synthesis conditions or other ligands (for example trimesic acid, naphthalene-1,4-dicarboxylic acid, benzene-1,2, 4,5 tetracarboxylic acid) [20]. The synthesis of aluminum carboxylates with trimesic acid in the presence of DMF solvent (N,N'-dimethylformamide) [21], with fumaric acid [22] or with mixed carboxylates of aluminum and another metal (for example Ti, Mg, La, Mo) [23]. Finally, a Norwegian patent of the university of Oslo [24] also sets forth the preparation of MIL-53 type solids from terephthalic acid functionalized with amino groups (—$NH_2$).

Among the various families of studied compounds, that incorporating aluminum is more particularly sought by industries owing to the low production cost of this kind of materials. Moreover, as a light element, the aluminum based materials may have high storage capacities for molecules such as $H_2$, $CH_4$, $CO_2$, etc To date, among the known processes for preparing MOFs, in particular aluminum based MOFs, no process describes the preparation of MOF materials containing aluminum azocarboxylate ligands. Neither have the structure of these materials and the topology of the constituting elements been studied in the prior art.

However, surprisingly, crystallized aluminum azocarboxylate based MOFs proved to be particularly interesting in terms of porosity and purity.

Generally, it is difficult to control the structural organization and the porosity of MOF materials. This can for example be related to the risks of interpenetration and interleaving of the frameworks during the formation of these materials which can lead to a dense material with reduced pores. Thus, the obtained material can exhibit a heterogeneous structure with inappropriate porosity.

Therefore, it would be interesting to be able to prepare aluminum azocarboxylate based MOFs for which the structures can be controlled in order to obtain specific properties in particular a crystallized structure, a customized pore diameter, adapted to the molecules to be adsorbed, an improved specific surface area and/or adsorption capacity, etc.

In addition, aluminum based MOF solids obtained by the majority of known processes may not be adapted to the desired application as they may include several phases, be in amorphous form or contain undesirable secondary substances obtained and not eliminated during the preparation of the MOF solids. Moreover, said solids do not always exhibit a sufficient porosity, and thus a sufficient adsorption capacity. To date, no methods exist for preparing aluminum azocarboxylate MOFs which can provide MOF type aluminum azocarboxylates having the required purity, porosity and crystallinity properties, with a good yield.

Thus, there exists a real need for a method for preparing aluminum azocarboxylates of metal-organic framework, MOF, type, which may be reproduced, and is industrially applicable.

Moreover, there exists a real need for a method for preparing MOF type aluminum azocarboxylates which, without resorting to additional steps in particular purification and/or crystallization steps, can lead to a crystallized MOF solid, made up of a single phase, highly pure (free from any secondary product) and exhibiting a sufficient porosity adapted to the use for which the MOF is intended.

DESCRIPTION OF THE INVENTION

The purpose of the present invention is precisely to meet this requirement by providing a method for preparing a MOF solid of a crystallized and porous aluminum aromatic azocarboxylate, including at least the following steps of:
(i) mixing in a non-aqueous organic solvent:
at least a metal inorganic precursor in the form of a metal Al, a metal salt $Al3^+$ or a coordination complex including metal ion $Al3^+$; and
at least an organic precursor of the ligand L, L being an aromatic azodi-, azotri-, azotetra-carboxylate ligand of formula $R^0R^1N_2$ $(COO^-)_q$ where $R^0$ and $R^1$ independently from each other, represent,
a mono- or poly-cyclic, fused or non fused, aryl radical, including 6 to 50 carbon atoms, for example 6 to 27 carbon atoms,
a mono- or poly-cyclic, fused or non fused, heteroaryl radical including 4 to 50 carbon atoms, for example 4 to 20 carbon atoms,
the $R^0$ radical being optionally substituted by one or more groups independently selected from the group including $C_{1-10}$ alkyl, $C_{2-10}$ alkene, $C_{2-10}$ alkyne, $C_{3-10}$ cycloalkyl, $C_{1-10}$ heteroalkyl, $C_{1-10}$ haloalkyl, $C_{6-10}$ aryl, $C_{3-20}$ heterocyclic, $C_{6-10}$ aryl $C_{1-10}$ alkyl, $C_{5-10}$ heteroaryl $C_{1-10}$ alkyl, F, Cl, Br, I, —$NO_2$, —CN, —$CF_3$, —$CH_2CF_3$, —OH, —$CH_2OH$, —$CH_2CH_2OH$, —$NH_2$, —$CH_2NH_2$, —NHCHO, —COOH, —$CONH_2$, —$SO_3H$, —$PO_3H_2$,
q=2 to 4;
(II) heating the mixture obtained in (i) at a temperature of at least 50° C. so as to obtain said solid.

In the frame of the present invention the terms "crystallized solid" and "crystalline solid" may be indifferently used to indicate a solid in which the atoms, the ions or the molecules form long distance ordered arrangements in the three space dimensions, leading to a single signature composed of a specific succession of diffraction peaks (X-rays for example) for each solid.

An "amorphous solid" is a solid where the atoms, ions or molecules, although locally ordered, disorderly stack up at long distance. This leads to a signature of one or more very wide diffraction peaks (X-rays for example) preventing a precise identification of the material (as several solids can coexist and lead to the same diffraction signature).

In many solids, the atoms, ions or molecules can adopt several arrangements according to their formation conditions. These different arrangements constitute the various existing "phases" of the solid in a given chemical system. The physical properties like the melting point and the density of the various phases are distinguished, permitting the differentiation of the solids.

within the meaning of the present invention, what is meant by "alkyl" is a saturated, optionally substituted, linear or branched carbon radical including 1 to 12 carbon atoms, for example 1 to 10 carbon atoms, for example 1 to 8 carbon atoms, for example 1 to 6 carbon atoms.
For example, an alkyl radical may be a methyl, ethyl, n-propyl, isopropyl, n-butyl, sec-butyl, isobutyl, tert-butyl, n-pentyl, sec-pentyl, isopentyl, tert-pentyl, n-hexyl, sec-hexyl radical or like radicals.

Within the meaning of the present invention, what is meant by "alkene" is a linear or branched, cyclic or acyclic, unsaturated hydrocarbon radical including at least a double carbon-carbon bond. The alkenyl radical may comprise 2 to 20 carbon atoms, for example 2 to 10 carbon atoms, more particularly 2 to 8 carbon atoms, even more particularly 2 to 6 carbon atoms. For example, an alkenyl radical may be an allyl, ethenyl, propenyl, butenyl, 1-methyl-2-buten-1-yl radical or like radicals.

The term "alkyne" designates a linear or branched, cyclic or acyclic unsaturated hydrocarbon radical, including at least a triple carbon-carbon bond. The alkynyl radical may comprise 2 to 20 carbon atoms, preferably 2 to 10 carbon atoms, more particularly 1 to 8 carbon atoms, even more particularly 2 to 6 carbon atoms. For example, an alkynyl radical may be an ethynyl, 2-propynyl (propargyl), 1-propynyl radical or like radicals.

Within the meaning of the present invention, what is meant by "aryl" is an aromatic system including at least a ring satisfying Hückel's aromaticity rule. Said aryl is optionally substituted and may comprise from 6 to 50 carbon atoms, for example 6 to 27 carbon atoms, in particular 6 to 14 carbon atoms, more particularly 6 to 12 carbon atoms. For example, an aryl radical may be a phenyl, naphthyl, tetrahydronaphthyl, indanyl, indenyl group or like radicals.

within the meaning of the present invention, what is meant by "heteroaryl", is a system including at least an aromatic ring of 4 to 50 carbon atoms, for example 4 to 20 carbon atoms, and at least a heteroatom selected from the group including in particular sulfur, oxygen, nitrogen. Said heteroaryl may be substituted. For example, a heteroaryl radical may be a pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl radical and like radicals.

Within the meaning of the present invention, what is meant by "cycloalkyl" is a cyclic, saturated or unsaturated, optionally substituted carbon radical, which may comprise 3 to 10 carbon atoms. For example, cyclopropyl, cyclobutyl, cyclopentyl, cyclohexyl, cycloheptyl, cyclooctyl, 2-methylcyclobutyl, 2,3-dimethylcyclobutyl, 4-methylcyclobutyl, 3-cyclopentylpropyl may be mentioned.

Within the meaning of the present invention, what is meant by "haloalkyl" is an alkyl radical such as previously defined, said alkyl system including at least a halogen selected from the group including fluorine, chlorine, bromine, iodine.

Within the meaning of the present invention, what is meant by "heteroalkyl", is an alkyl radical such as previously defined, said alkyl system including at least a heteroatom, particularly, a heteroatom selected from the group including sulfur, oxygen, nitrogen, phosphorus.

Within the meaning of the present invention, what is meant by "heterocycle" is a saturated or unsaturated, optionally substituted, cyclic carbon radical including at least a heteroatom and which may comprise 3 to 20 carbon atoms, preferably 5 to 20 carbon atoms, preferably 5 to 10 carbon atoms. The heteroatom may be for example selected from the group including sulfur, oxygen, nitrogen, phosphorus. For example, a heterocyclic radical may be a pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, or tetrahydrofuryl group.

Within the meaning of the present invention, what is meant by "alkoxy", "aryloxy", "heteroalkoxy" and "heteroaryloxy", respectively, is an alkyl, aryl, heteroalkyl and heteroaryl radical bonded to an oxygen atom. For example, an alkoxy radical may be a methoxy, ethoxy, propoxy, isopropoxy, n-butoxy, tert-butoxy, neopentoxy, n-hexoxy radical or like radicals.

The term "substituted" designates for example the replacement of a hydrogen atom in a structure given by a group such as previously defined. When more than one position can be substituted, the substituents may be same or different at each position.

In the context of the invention, the organic solvent can be made up of only one solvent or a mixture of organic solvents.

The term "nonaqueous solvent" advantageously refers to a solvent or a mixture of solvents containing up to 5 wt %, preferably 1 wt %, more preferably 0.1 wt % and even more preferably up to 0.01 wt % of water with respect to the total weight of all solvents.

The nonaqueous organic solvent can be selected from the group including N,N-dimethylformamide (DMF), N,N-diethylformamide (DEF), dioxane, methanol, ethanol, n-propanol, isopropanol, n-butanol, isobutanol, tert-butanol, cyclohexanol, pyridine, toluene, ethyl acetate, dimethyl sulfoxide (DMSO).

The nonaqueous organic solvent is more particularly selected from the group including DMF, DEF, dioxane, methanol, ethanol, DMSO.

The metal inorganic precursor in step (i) may be a metal Al, metal salt $Al^{3+}$ or a coordination complex including metal ion $Al^{3+}$. When it is metal salt, the counter-ion may be an inorganic ion selected from the group including sulfate, nitrate, nitrite, sulphite bisulfite, phosphate, phosphite, fluoride, chloride, bromide, iodide, perchlorate, carbonate, bicarbonate. The counter-ion may also be an organic ion selected from the group including acetates, formates, oxalates, citrates, ethoxy, isoproxy. Preferably, the metal inorganic precursor is a metal salt $Al^{3+}$.

The crystalline spatial organization of the solids of this invention forms the basis of the particular characteristics and features of these materials. In particular, it governs the size of the pores, which affects the specific surface area of the materials and the adsorption characteristics. It also governs the density of the materials which is relatively weak, the proportion of metal in these materials, the stability of the materials, the rigidity and the flexibility of the structures, etc Moreover, the pore size may be adjusted by the choice of appropriate Ligands L. In the method of the invention, the Ligand L is more particularly an aromatic azodi- or azotetracarboxylic ligand, selected from the group including:

$C_{12}H_8N_2(CO_2^-)_2$ (azobenzene-4,4'-dicarboxylate),
$C_{12}H_6Cl_2N_2(CO_2^-)_2$ (dichloro-azobenzene-4,4'-dicarboxylate),
$C_{12}H_6N_2(CO_2^-)_4$ (azobenzene-3,3',5,5'-tetracarboxylate),
$C_{12}H_6N_2(OH)_2(CO_2^-)_2$ (dihydroxy-azobenzene-4,4'-dicarboxylate).

In step (i) the metal inorganic precursor and the organic precursor of the Ligand L can be mixed in a molar ratio comprised between 1 and 5.

As already indicated, MOF solids according to the invention have a crystallized structure which provides these materials with specific properties. In the method according to the invention, crystallization is carried out in a precise temperature range. Thus, in step (ii), the mixture is heated at a temperature ranging from 50° C. to 150° C. The mixture may be heated for 1 to 10 days. One day corresponds to 24 hours. The mixture may be heated in a closed cell.

Step (ii) may be carried out with an autogenous pressure higher than $10^5$ Pa. An "autogenous" pressure corresponds to the pressure generated by the reagents at a given temperature in a closed reaction cell.

The solid obtained at the end of step (ii) may be further subjected to an activation step (iii) in which said solid is heated at a temperature of 100° C. to 300° C., preferably of 100° C. to 200° C. In this step, the solid may be heated for 1 to 48 hours.

The activation step (iii) may be optionally carried out in a mixture of solvent(s) selected from the group including DMF, DEF, methanol, ethanol, DMSO or water.

With this activation step (iii) it is particularly possible to empty the pores of the MOF solid of the invention and make them available for the intended use of said solid. Emptying can be done, for example, by the departure of the water, solvent molecules and/or if necessary, of the molecules of Ligands L present in the reaction medium. Resulting MOF solids will then have a stronger adsorption and storage capacity.

The object of the present invention is also an MOF solid of a crystallized and porous aluminum aromatic azocarboxylate that may be obtained by the method according to the invention, including a three-dimensional succession of patterns of formula (I):

$$Al_mO_kX_lL_p \qquad (I)$$

in which:
Al represents the metal ion $Al^{3+}$;
m is 1 to 15, for example 1 to 8;
k is 0 to 15, for example 1 to 8;
l is 0 to 10, for example 1 to 8;
p is 1 to 10, for example 1 to 5;
m, k, l and p are selected so as to respect the neutrality of the charges of said pattern;
X is an anion selected from the group including $OH^-$, $Cl^-$, $F^-$, $I^-$, $Br^-$, $SO_4^{2-}$, $NO_3-$, $ClO_4^-$, $PF_6^-$, $BF_3^-$, $R^2$—$(COO^-)_n$, $R^2$—$(SO_3^-)_n$, $R^2$—$(PO_3^-)_n$, where $R^2$ is hydrogen, linear or branched, optionally substituted $C_{1-12}$ alkyl, n=1 to 4;
L is a ligand such as previously defined.

Aluminum aromatic azocarboxylate MOF solids prepared by the method of the invention exhibit some advantages of which:
they are crystallized solids,
they are highly pure (no secondary product such as for example aluminum hydroxyl is detected), and
the exhibit a significant porosity (Langmuir surface up to 3500 m²/g) allowing to particularly control the adsorption characteristics of certain molecules.

Preferably, X is selected from the group including $OH^-$, $Cl^-$, $F^-$, $ClO_4^-$.

MOF Solids according to the invention preferably comprise Al from 5 to 50% in wt %.

MOF Solids that may be obtained by the method of the invention have pores, and more particularly micro- and/or meso-pores. The micropores can be defined as pores having a diameter lower than or equal to 2 nm (diameter≤2 nm) and the mesopores as pores having a diameter higher than 2 nm and that up to 50 nm (2 nm<diameter<50 nm). Preferably, the diameter of the pores of the MOF solid of the invention ranges from 0.2 to 6 nm. The presence of micro- and meso-pores may be followed by sorption measurements so as to determine the capacity of the MOF solid to absorb nitrogen at 77K according to DIN 66131.

The specific surface area of the solids made up of porous and crystallized aluminum aromatic azocarboxylate MOFs, that may be obtained by the method of the invention, may be measured by the BET method and determined and calculated by the Langmuir model. Said solids may have a BET surface area from 50 to 4200 m²/g, more particularly from 100 to 3000 m²/g. They may also have a Langmuir surface area from 50 to 6000 m²/g, more particularly from 150 to 3500 m²/g.

MOF solids according to the invention advantageously have a porous volume of 0.3 to 4 cm$^3$/g. Within the framework of the invention, porous volume means the volume accessible for gas or liquid molecules.

Within the framework of this invention, MOF solids may have a gas load capacity from 0.5 to 50 mmol of gas per gram of dry solid. The load capacity means the gas storage capacity or the quantity of gas adsorbed by the solid. These values and this definition also apply to the load capacity of liquids.

MOF solids of this invention may particularly exhibit the advantage of a thermal stability up to a temperature of 500° C. More particularly, these solids may have a thermal stability between 250° C. and 450° C.

MOF solids of the invention are crystallized and may preferably be in the form of crystallites with a length which varies from 0.05 to 100 μm, more particularly from 0.05 to 20 μm. They are preferably in the form of small crystals having a particular morphology (needles, plates, octahedral, etc.) also permitting their precise identification by examination through a scanning electron microscope (SEM).

As already indicated, MOF solids according to the invention have a crystallized structure and are highly pure providing these materials with specific properties.

Contrary to the known solids, aluminum azocarboxylate MOF solids according to the invention are composed of a single phase. That means that the other phases that may exist in the considered chemical system are not present mixed with the solid.

Moreover, aluminum azocarboxylate MOF solids that may be obtained by a preparation process as previously described, exhibit a degree of purity of at least 95%, in particular at least 98 mass %. The purity of MOF solids of the invention may be in particular determined by elementary chemical analysis, X-rays diffraction, scanning electron microscopy. Thus, the obtained MOF solids, do not comprise, or very little, secondary products such as for example aluminum hydroxide of formula Al(OH)$_3$ or AlO(OH) or the other phases of the considered chemical system appearing under other synthesis conditions.

The particular structural characteristics of the solids of the present invention make them high load capacity, highly selective, and highly pure adsorbents. Thus, they make the selective adsorption, and thus, the selective separation of gas molecules such as for example of NO, $N_2$, $H_2S$, $H_2$, $CH_4$, $O_2$, CO, $CO_2$ . . . ) molecules, possible.

The object of the present invention is also the use of a solid composed of crystallized and porous aluminum azocarboxylates MOF for the storage of liquid or gas molecules, for selective gas separation [25] or for catalysis [26].

Other advantages will become more apparent to the skilled person upon reading the examples below, illustrated by the accompanying figures, given by way of illustration.

EXAMPLES

Figure 1:
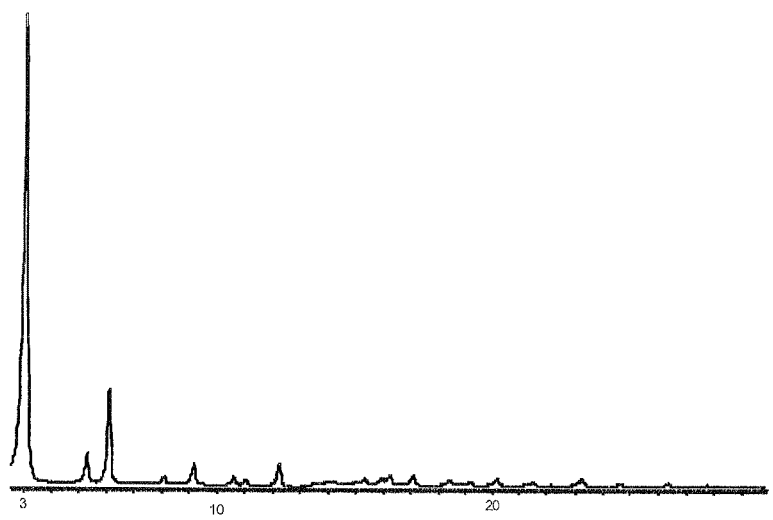
FIG. 1 represents the X-ray diffraction diagram of the phase MIL-130 (Al) (CuK$_D$). The X-coordinate represents the angular variation in 2D) (°). The ordinate represents the relative diffraction peak intensity.

The following examples describe the synthesis of solids made up of MOFs of microporous aluminum aromatic azocarboxylate (noted Mil-n) obtained with azobenzene carboxylate type ligands and more particularly with the azodibenzene-4,4'-dicarboxylate. The synthesized compounds (noted Mil-n) were then characterized by X-ray powder diffraction, by thermogravimetric analysis, scanning electron microscopy (SEM) and their specific surface areas were measured by the BET method.

The diffraction diagrams were recorded using a diffractometer (Siemens D5000) in Bragg-Brentano reflection geometry on an angular 2theta field of 2 to 40° with a pitch and a count time of 0.02° and 1 second, respectively (CuK$_{D1,2}$ radiation). The thermogravimetric analysis (TA Instrument 2050) was carried out from a sample of 5 or 20 mg heated on a balance at 20 to 600° C. under oxygen stream with a heating rate of 3° C.·min$^{-1}$. With regard to the examination with the scanning electron microscope (LEO 1530), the samples were metallized with carbon then placed in a vacuum room under the electron beam. The specific surface areas were measured on a Micromeritics ASAP2010 apparatus from 100 mg samples which were heated beforehand under vacuum at 200° C. for 12 hours.

Example 1

Preparation of MIL-130 (Al)

Compound MIL-130 (Al) is obtained from a mixture of 3.6 g of aluminum nitrate (Al(NO$_3$)$_3$.9H$_2$O), 1.2 g of azodibenzene-4,4'-dicarboxylic acid and 70 ml of DMF (N,N'-dimethylformamide) placed in a 125 ml Teflon cell then inserted in a Parr steel autoclave (registered trademark). The reaction takes place at 100° C. for 7 days in an oven. 2 g of MIL-130 (Al) are obtained. The product is activated by heating at 200° C. over night.

A second preparation may be prepared from a mixture of 0.36 g aluminum perchlorate (Al(ClO$_4$)$_3$.9H$_2$O), 0.1 g of azodibenzene-4,4'-dicarboxylic acid, 5 ml of DMF (N,N'-dimethylformamide) placed in a 23 ml Teflon cell then a Parr type steel autoclave (trade name). The reaction takes place at 100° C. for 7 days in an oven. 0.11 g of MIL-130 (Al) are obtained.

A third preparation may be prepared from a mixture of 0.19 g of aluminum chloride hexahydrate (Al(Cl)$_3$.6H$_2$O), 0.1 g of azodibenzene-4,4'-dicarboxylic acid, 5 ml of DMF (N,N'-dimethylformamide) placed in a 23 ml Teflon cell then a steel autoclave of trade name Parr (registered trademark). The reaction takes place at 100° C. for 7 days in an oven. 0.07 g of MIL-130 (Al) are obtained.

A fourth preparation may be prepared from a mixture of 0.1 g of anhydrous aluminum chloride (Al(Cl)$_3$), 0.1 g of azodibenzene-4,4'-dicarboxylic acid, 5 ml of DMF (N,N'-dimethylformamide) placed in a 23 ml Teflon cell then a steel autoclave of brand name Parr (registered trademark). The reaction takes place at 100° C. for 7 days in an oven. 0.07 g of MIL-130 (Al) are obtained.

A fifth preparation may be prepared from a mixture of 0.1 g of anhydrous aluminum chloride (Al(Cl)$_3$), 0.1 g of azodibenzene-4,4'-dicarboxylic acid, 5 ml of DMF (N,N'-dimethylformamide) placed in a 23 ml Teflon cell then a steel autoclave of brand name Parr (registered trademark). The reaction takes place at 100° C. for 4 hours in an oven. 0.07 g of MIL-130 (Al) are obtained.

Figure 4:
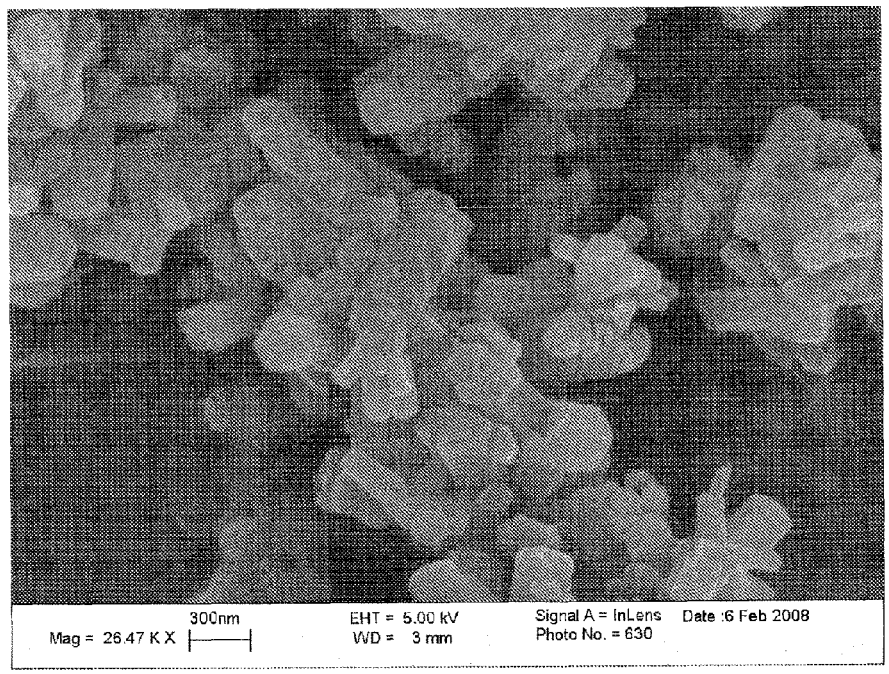
FIG. 4 represents the photography (scanning electron microscopy) of a sample of MIL-130 (Al) showing hexagonal rod shaped crystallites.
Figure 5:
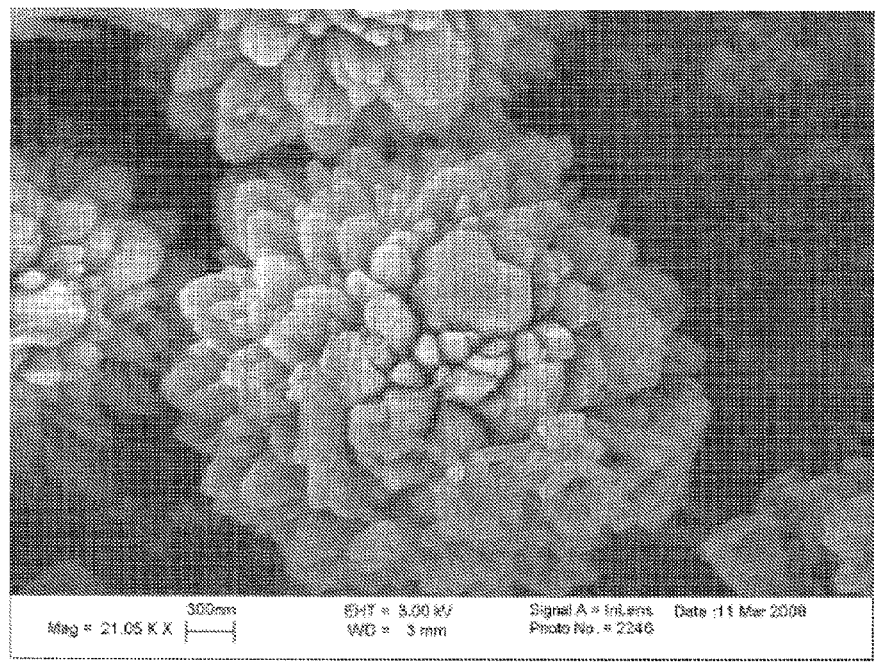
FIG. 5 represents the photography (scanning electron microscopy) of a sample of MIL-130 (Al) showing ovoid crystallite aggregates shaped crystallites.
Figure 6:
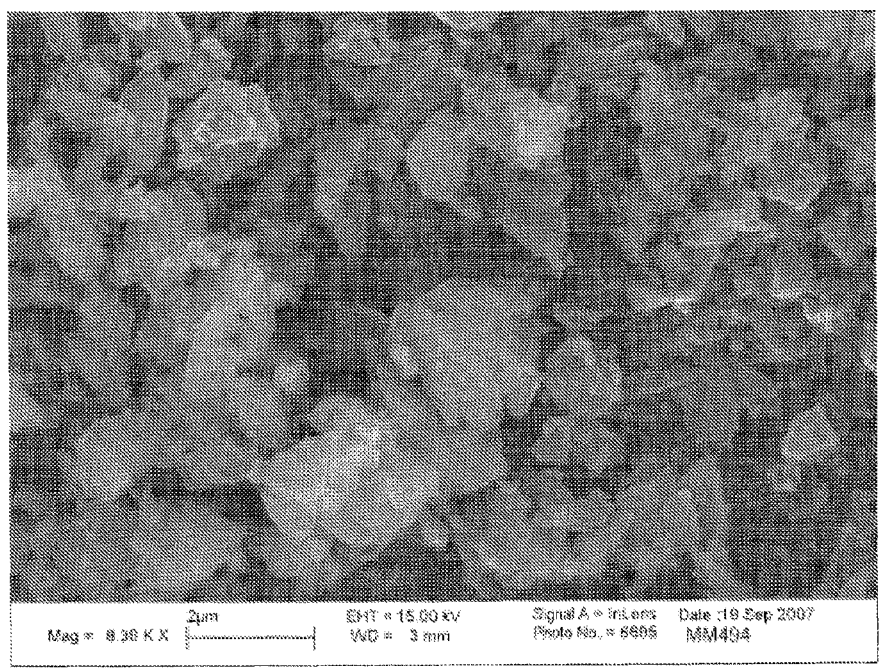
FIG. 6 represents the photography (scanning electron microscopy) of a sample of MIL-130 (Al) showing ovoid plates shaped crystallites.

The examination of these solids (for example, the fourth preparation) with the electron microscope shows the presence of small hexagonal rod-shaped crystals with a mean size of 0.2 to 0.8 microns (FIG. 4), of ovoid crystallite aggregates (FIG. 5) from the second preparation or of ovoid plates (FIG. 6) from the first preparation.

The Bragg peaks of the powder diagram may correspond to a hexagonal mesh with parameters a=b=33.264 (1) Å and C=4.681 (1) Å, V=4417.5 (1) Å$^3$. The X-ray Diffractogram is shown on FIG. 1.

Figure 2:
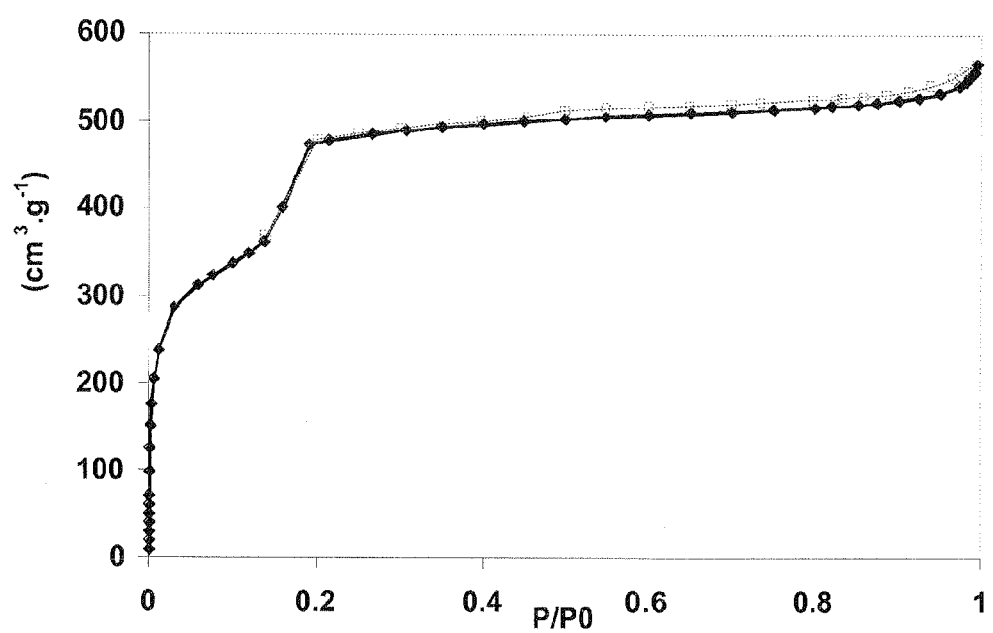
FIG. 2 represents the phase MIL-130 adsorption isotherm $N_2$ at 77K of. The ratio p/p$^0$ which corresponds to the relative pressure is given in X-coordinate. The volume of adsorbed gas per gram of product (cm$^3 \cdot$g$^{-1}$) is represented on the ordinate.
Figure 3:
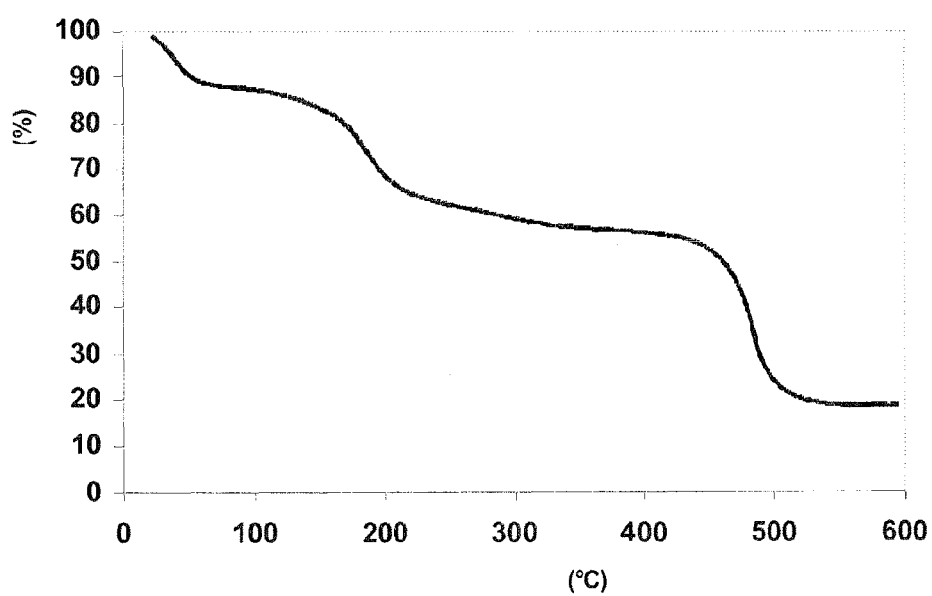
FIG. 3 represents the thermogravimetric analysis curve of MIL-130 (Al) (under $O_2$ stream, 3° C.·min$^{-1}$). The percentage of the mass loss is represented on the ordinate. The heating temperature is represented on the X-coordinate.

The BET surface area is of 1770 m$^2$/g and the Langmuir surface is of 3190 m$^2$/g. The adsorption isotherm exhibits a step for $p/p_0$=0.15, which is characteristic of mesoporous cavities or tunnels (FIG. 2). The thermogravimetric analysis indicates that the material MIL-100 (Al) is stable up to 420° C. (FIG. 3).

The combination of these various characterization analyses (XRD, SEM) shows that it is a very well identified material with a high crystalline purity. Following the XRD observation, a compound, for which phase MIL-130 (Al) represents the major part at least up to 95% (in mass) may be defined.

LIST OF REFERENCES

[1] Reticular Synthesis and the Design of New Materials, O. M. Yaghi, M. O'Keeffe, N. W. Ockwig, H. K. Chae, M. Eddaoudi and J. Kim, *Nature*, 423, 705-14 (2003).

[2] Functional Porous Coordination Polymers, S. Kitagawa, R. Kitaura and S.-l. Noro, *Angew. Chem. Int. Ed.*, 43, 2334-75 (2004).

[3] Hybrid Porous Solids: Past, Present, Future, G. Férey, *Chem. Soc. Rev.*, 37, 191-214 (2008).

[4] Hydrogen Storage in Microporous Metal-Organic Frameworks, N. L. Rosi, J. Eckert, M. Eddaoudi, D. T. Vodak, J. Kim, M. O'Keeffe and O. M. Yaghi, *Science*, 300, 1127-9 (2003).

[5] Hydrogen Adsorption in the Nanoporous Metal-benzenedicarboxylate M(OH) ($O_2C-C_6H4-CO_2$) (M=$Al^{3+}$, $Cr^{3+}$), MIL-53, G. Férey, M. Latroche, C. Serre, F. Millange, T. Loiseau and A. Percheron-Guéegan, *Chem. Commun.*, 2976-7 (2003).

[6] Hydrogen Storage in the Giant-Pore Metal-Organic Frameworks MIL-100 and MIL-101, M. Latroche, S. Surblé, C. Serre, C. Mellot-Draznieks, P. L. Llewellyn, J.-H. Lee, J.-S. Chang, S. H. Jhung and G. Férey, *Angew. Chem. Int. Ed.*, 45, 8227 (2006).

[7] Systematic Design of Pore Size and Functionality in Isoreticular MOFs and their Application in Methane Storage, M. Eddaoudi, J. Kim, N. Rosi, D. Vodak, J. Wächter, M. O'Keeffe and O. M. Yaghi, *Nature*, 295, 469-72 (2002).

[8] Different Adsorption Behaviors of Methane and Carbon Dioxide in the Isotypic Nanoporous Metal Terephthalates MIL-53 and MIL-47, S. Bourrelly, P. L. Llewellyn, C. Serre, F. Millange, T. Loiseau and G. Férey, *J. Am. Chem. Soc*, 127, 13519-21 (2005).

[9] Metal-Organic Frameworks as Efficient Materials for Drug Delivery, P. Horcajada, C. Serre, M. Vallet-Regi, M. Sebban, F. Taulelle and G. Férey, *Angew. Chem. Int. Ed.*, 45, 5974 (2006).

[10] High Gas Adsorption in a Microporous Metal-Organic Framework with Open-Framework, O. M. Yaghi, WO 2006/110740 (2006).

[11] Isoreticular Metal-Organic Framework Process for Forming the Same and Systematic Design of Pore size and Functionality therein, with Application for Gas Storage, WO 02/088148 (2002).

[12] Metal-Organic Frameworks—Prospective Industrial Applications, U. Müller, M. Schubert, F. Teich, H. Pütter, K. Schierle-Arndt and J. Pastre, *J. Mater. Chem.*, 16, 626-36 (2006).

[13] Shaped Bodies Containing Metal-Organic Frameworks, M. Hesse, U. Müller, O. M. Yaghi, WO 2006/050898 (2006).

[14] A Rationale for the Large Breathing of the Porous Aluminum Terephthalate (MIL-53) Upon Hydration, T. Loiseau, C. Serre, C. Huguenard, G. Fink, F. Taulelle, M. Henry, T. Bataille and G. Férey, *Chem. Eur. J.*, 10, 1373-82 (2004).

[15] Hydrothermal Synthesis and Crystal Structure of a New Three-Dimensional Aluminum-Organic Framework MIL-69 with 2,6-Naphthalenedicarboxylate (ndc), Al(OH)(ndc)QH$_2$O, T. Loiseau, C. Mellot-Draznieks, H. Muguerra, G. Férey, M. Haouas and F. Taulelle, C. R. Chimie, *Special Issue on Crystalline and Organized Porous Solids*, 8, 765-72 (2005).

[16] MIL-96, a Porous Aluminum Trimesate 3D Structure Constructed from a Hexagonal Network of 18-Membered Rings and $\mu_3$-0×0-Centered Trinuclear Units, T. Loiseau, L. Lecroq, C. Volkringer, J. Marrot, G. Férey, M. Haouas, F. Taulelle, S. Bourrelly, P. L. Llewellyn and M. Latroche, *J. Am. Chem. Soc*, 128, 10223-30 (2006).

[17] A Microdiffraction Set-up for Nanoporous Metal-Organ ic-Framework-Type Solids, C. Volkringer, D. Popov, T. Loiseau, N. Guillou, G. Férey, M. Haouas, F. Taulelle, C. Mellot-Draznieks, M. Burghammer and C. Riekel, *Nature Matehals*, 6, 760-4 (2007).

[18] Design and Synthesis of an Exceptionally Stable and Highly Porous Metal-Organic Framework. H. Li, M. Eddaoudi, M. O'Keeffe, O. M. Yaghi, *Nature*, 402, 276-9 (1999).

[19] A Chemically Functionalizable Nanoporous Material [$Cu_3(TMA)_2(H_2O)_3$]$_n$, S. S.-Y. Chui, S. M.-F. Lo, J. P. H. Charmant, A. Guy Orpen and I. D. Williams, *Science*, 283, 1148 (1999).

[20] Method for Producing Organometallic Framework Materials Containing Main Group Metal Ions, M. Schubert, U. Müller, M. Tonigold, R. Ruetz, WO 2007/023134 (2007).

[21] Mesoporous Metal-Organic Framework, M. Schubert, U. Müller, H. Mattenheimer, M. Tonigold, WO 2007/023119 (2007).

[22] Organometallic Aluminum Fumarate Backbone Material, C. Kiener, U. Müller, M. Schubert, WO 2007/118841 (2007).

[23] Dotierte Metallorganische Gerüstmaterialien, M. Schubert, U. Müller, R. Ruetz, S. Hatscher, DE 10 2005 053 430 (2005).

[24] MOF-Compounds as Gas Adsorbers, K. O. Kongshaug, R. H. Heyn, H. Fjellvag, R. Blom, WO 2007/128994 (2007).

[25] <<How hydration drastically improves adsorption selectivity for CO2 over CH$_4$ in the flexible Chromium terephtalate MIL-53>>, P. L. Llewellyn, S. Bourrelly, C. Serre, Y. Filinchuk and G. Férey, Angew. Chem. Int. Ed. 45 7751-4 (2006).

[26] <<Synthesis and catalysis properties of MIL-100(Fe), an iron(111) carboxylate with large pores>> P. Horcajada, S. Surble, C. Serre, D.-Y. Hong, Y.-K. Seo, J.-S Chang, J.-M. Greneche, I. Margiolaki and G. Férey, Chem. Commun. 2820-2 (2007); <<Catalytic properties of MIL-101>> A. Henschel, K. Gedrich, R. Kraehnert and S. Kaskel, Chem. Commun. 4192-4 (2008); <<Amine grafting on coordinatively unsaturated metal centers of MOFs: consequences for catalytis and metal encapsulation>> Y. K. Hwang, D.-Y. Hong, J.-S. Chang, S. H. Jhung, Y.-K. Seo, J. Kim, A. Vimont, M. Daturi, C. Serre and G. Férey, Angew. Chem. Int. Ed. 47 4144-8 (2008).

The invention claimed is:

1. A method for preparing a MOF solid of porous and crystallized aluminum aromatic azocarboxylate, comprising:
   (i) mixing in a nonaqueous organic solvent:
      at least a metal inorganic precursor in the form of a metal Al, a metal salt $Al^{3+}$ or a coordination complex comprising metal ion $Al^{3+}$; and
      at least an organic precursor of ligand L, L comprising an aromatic azodi-, azotri-, or azotetra-carboxylate ligand of formula $R^0R^1N_2 (COO^-)_q$ where $R^0$ and $R^1$ independently from each other represent
         a mono- or poly-cyclic, fused or non fused, aryl radical, comprising 6 to 50 carbon atoms,
         a mono- or poly-cyclic, fused or non fused, heteroaryl radical comprising 4 to 50 carbon atoms,
            the $R^0$ radical being optionally substituted by one or more groups independently selected from the group consisting of $C_{1-10}$ alkyl, $C_{2-10}$ alkene, $C_{2-10}$ alkyne, $C_{3-10}$ cycloalkyl, $C_{1-10}$ heteroalkyl, $C_{1-10}$ haloalkyl, $C_{6-10}$ aryl, $C_{3-20}$ heterocyclic, $C_{6-10}$ aryl $C_{1-10}$ alkyl, $C_{5-10}$ heteroaryl $C_{1-10}$ alkyl, F, Cl, Br, I, —$NO_2$, —CN, —$CF_3$, —$CH_2CF_3$, —OH, —$CH_2OH$, —$CH_2CH_2OH$, —$NH_2$, —$CH_2NH_2$, —NHCHO, —COOH, —$CONH_2$, —$SO_3H$, and —$PO_3H_2$, and
   q=2 to 4; and
   (ii) heating the mixture obtained in (i) at a temperature of at least 50° C. so as to obtain said solid.

2. The method according to claim 1, wherein the nonaqueous organic solvent is selected from the group consisting of DMF, DEF, dioxane, methanol, ethanol, and DMSO.

3. The method according to claim 1, wherein in step (i) the metal inorganic precursor and the organic precursor of the ligand L are mixed in a molar ratio comprised between 1 and 5.

4. The method according to claim 1, wherein the metal inorganic precursor is in the form of a metal salt $Al^{3+}$.

5. The method according to claim 1, wherein L is an aromatic azodi- or azotetra-carboxylic ligand, selected from the group consisting of:
   $C_{12}H_8N_2(CO_2^-)_2$(azobenzene-4,4'-dicarboxylate),
   $C_{12}H_6Cl_2N_2(CO_2^-)_2$(dichloro-azobenzene-4,4'-dicarboxylate),
   $C_{12}H_6N_2(CO_2^-)_4$(azobenzene-3,3',5,5'-tetracarboxylate), and
   $C_{12}H_6N_2(OH)_2(CO_2^-)_2$(dihydroxy-azobenzene-4,4'-dicarboxylate).

6. The method according to claim 1, wherein in step (ii) the mixture is heated at a temperature of 50° C. to 150° C.

7. The method according to claim 1, wherein in step (ii) the mixture is heated for 1 to 10 days.

8. The method according to claim 1, wherein step (ii) is carried out at an autogenous pressure higher than $10^5$ Pa.

9. The method according to claim 1, further comprising an activation step (iii) in which the solid obtained in (ii) is heated at a temperature of 100 to 300° C.

10. The method according to claim 9, wherein the activation step (iii) is carried out in a mixture of solvents selected from the group consisting of DMF, DEF, methanol, ethanol, DMSO, and water.

11. The method according to claim 9, wherein in activation step (iii) the solid obtained in step (ii) is heated for 1 to 48 hours.

* * * * *